US011524083B1

(12) United States Patent
Potthast (10) Patent No.: US 11,524,083 B1
(45) Date of Patent: Dec. 13, 2022

(54) PERSONAL, PORTABLE, HAND-HELD UV SANITIZER AND METHOD OF USE

(71) Applicant: James William Potthast, Woodstock, IL (US)

(72) Inventor: James William Potthast, Woodstock, IL (US)

( * ) Notice: Subject to any disclaimer, the term of this patent is extended or adjusted under 35 U.S.C. 154(b) by 0 days.

(21) Appl. No.: 17/246,675

(22) Filed: May 2, 2021

Related U.S. Application Data

(60) Provisional application No. 63/047,163, filed on Jul. 1, 2020, provisional application No. 63/038,851, filed
(Continued)

(51) Int. Cl.
*A61L 2/00* (2006.01)

(52) U.S. Cl.
CPC ......... *A61L 2/0047* (2013.01); *A61L 2202/11* (2013.01); *A61L 2202/14* (2013.01); *A61L 2202/16* (2013.01)

(58) Field of Classification Search
CPC ............... A61L 2/0047; A61L 2202/11; A61L 2202/14; A61L 2202/16
See application file for complete search history.

(56) References Cited

U.S. PATENT DOCUMENTS

| 4,786,812 A | 11/1988 | Humphreys |
| D358,637 S | 5/1995 | Boehme |

(Continued)

FOREIGN PATENT DOCUMENTS

| CN | 108785863 A | 11/2018 |
| CN | 110694089 A | 1/2020 |

(Continued)

OTHER PUBLICATIONS

Author: Michael Hemsworth; "Smart Phone Mounted UV-C Santizers"; Published by Trend Setter on Jul. 16, 2020 in Tornto, Canada.
(Continued)

*Primary Examiner* — Sean E Conley
(74) *Attorney, Agent, or Firm* — James William Potthast (57) ABSTRACT

A personal, portable, handheld UV light sanitizer (20) having a tubular housing (22) with a UV light source (32) for uniformly radiating a user's hand through a light transmittable outer wall (24) of the housing having a girth and length that enables substantially the entire the exterior surface of the outer wall to be covered by a user's hand when fully grasping the outer wall. A rearward annular wall (41) reduces any rearward light leakage and provides a bearing surface against which the edge of the user's hand may rest to prevent slippage. An annular forward wall (40) reduce forward light leakage and mounts actuation switches (36, 56), remote sensors (58, 60), a status indicator light (61) and an alarm speaker (59). When the skin surface sanitization mode switch (36) is actuated, skin sanitizing UV light radiation (42) radiates the inside of the user's hand for a preselected time period, unless there have previously been an excessive number of past hand sanitization cycles or too little time has passed since the last hand sanitization cycle (FIG. 9). Once energization, it is automatically deenergized after a preselected maximum time period (FIG. 9). Mounted to the front of the forward annular wall is another UV light source (51) that radiates UV light to suspect target surfaces spaced from the user's hand. A range finder (58) helps the user to hold the surface UV light source at the right distance from the target surface for effective sanitization, and energization is immediately terminated in response to an infrared sensor detecting that the surface UV light source is directed at a person's skin.

33 Claims, 5 Drawing Sheets

Related U.S. Application Data on Jun. 14, 2020, provisional application No. 63/030,368, filed on May 27, 2020, provisional application No. 63/024,254, filed on May 13, 2020.

(56) References Cited

U.S. PATENT DOCUMENTS

| | | | |
|---|---|---|---|
| 5,666,410 A | 9/1997 | McLane | |
| D428,503 S | 6/2000 | Rann et al. | |
| 6,132,897 A | 10/2000 | Chen | |
| 6,254,625 B1 | 7/2001 | Resenthal et al. | |
| 6,579,495 B1 | 6/2003 | Maiden | |
| 7,246,920 B1 | 7/2007 | Hopkins | |
| 7,250,615 B1 | 7/2007 | Soong et al. | |
| D581,058 S | 11/2008 | Elkerbout | |
| D629,529 S | 12/2010 | Russell, II et al. | |
| 9,265,850 B2 | 2/2016 | Davis et al. | |
| 9,572,903 B2 | 2/2017 | Dobrinnsk et al. | |
| 9,687,577 B2 | 6/2017 | Dobrinsky et al. | |
| 10,543,290 B2 | 1/2020 | Shur et al. | |
| 10,639,387 B2 | 5/2020 | Bonutti et al. | |
| 10,697,164 B1 | 6/2020 | Al-Sabah et al. | |
| 10,849,995 B2 | 12/2020 | Crosby | |
| 10,940,220 B2 | 3/2021 | Crosby et al. | |
| 2001/0042842 A1* | 11/2001 | Leighley | A61L 2/10 250/504 H |
| 2004/0034398 A1 | 2/2004 | Eckhardt et al. | |
| 2004/0256581 A1 | 12/2004 | Au et al. | |
| 2006/0078484 A1 | 4/2006 | Greep | |
| 2006/0079948 A1 | 4/2006 | Dawson et al. | |
| 2006/0212099 A1 | 9/2006 | Riddell | |
| 2007/0055195 A1 | 3/2007 | Browne | |
| 2008/0253941 A1 | 10/2008 | Wichers et al. | |
| 2009/0196622 A1 | 8/2009 | Shin et al. | |
| 2009/0230321 A1 | 8/2009 | Chen | |
| 2010/0114266 A1 | 5/2010 | Lechtwhaler | |
| 2010/0222852 A1 | 9/2010 | Vasily et al. | |
| 2011/0004280 A1 | 1/2011 | Irwin | |
| 2012/0085927 A1 | 4/2012 | Maeng et al. | |
| 2012/0156094 A1 | 6/2012 | Gordon | |
| 2012/0262912 A1* | 10/2012 | Wong | H01J 61/35 362/217.1 |
| 2013/0013932 A1 | 1/2013 | Irwin | |
| 2014/0319374 A1 | 10/2014 | Chandler | |
| 2015/0090903 A1* | 4/2015 | Cole | A61L 2/10 250/492.1 |
| 2015/0174426 A1 | 6/2015 | St. Germain et al. | |
| 2016/0030612 A1 | 2/2016 | Kim et al. | |
| 2016/0184467 A1 | 6/2016 | Cheng-Miooge et al. | |
| 2017/0080116 A1 | 3/2017 | Kreiner et al. | |
| 2017/0080117 A1 | 3/2017 | Gordon | |
| 2017/0080251 A1 | 4/2017 | Yehezkel | |
| 2017/0157276 A1 | 6/2017 | Dobrinsky et al. | |
| 2017/0216466 A1 | 8/2017 | Dujowich et al. | |
| 2018/0071414 A1 | 3/2018 | Dujowhich et al. | |
| 2018/0207302 A1 | 7/2018 | Vasilnko | |
| 2018/0343847 A1 | 12/2018 | Ervin | |
| 2019/0070325 A1 | 3/2019 | Preminger et al. | |
| 2019/0099613 A1 | 4/2019 | Estes et al. | |
| 2019/0117802 A1 | 4/2019 | Hishinuma et al. | |
| 2019/0172336 A1 | 6/2019 | Haidegger et al. | |
| 2019/0184044 A1* | 6/2019 | Yellen | A61L 2/10 |
| 2019/0240369 A1 | 8/2019 | Rotelli | |
| 2019/0255201 A1* | 8/2019 | Rosen | A61L 2/10 |
| 2019/0326105 A1 | 10/2019 | Matsumoto | |
| 2020/0030469 A1 | 1/2020 | Neister et al. | |
| 2020/0057181 A1 | 2/2020 | Yang et al. | |
| 2020/0069823 A1 | 3/2020 | Pangan, Jr. et al. | |
| 2020/0093030 A1 | 3/2020 | Yamakoshi et al. | |
| 2020/0108160 A1 | 4/2020 | Jung et al. | |
| 2020/0261611 A1 | 8/2020 | Bonutti et al. | |
| 2020/0261808 A1 | 8/2020 | Crosby et al. | |
| 2021/0196848 A1* | 7/2021 | Baarman | H02J 7/0042 |

FOREIGN PATENT DOCUMENTS

| | | |
|---|---|---|
| CN | 2105215540 U | 5/2020 |
| CN | 2114342266 U | 9/2020 |
| EP | 2465543 B1 | 1/2013 |
| EP | 3336817 B1 | 10/2019 |
| KR | 20200098104 A | 8/2020 |
| WO | 2016019367 A2 | 2/2016 |
| WO | WO2016019367 A3 | 2/2016 |
| WO | WO2019241112 A1 | 12/2019 |
| WO | WO202000838 A1 | 4/2020 |
| WO | WO2020083851 A1 | 4/2020 |

OTHER PUBLICATIONS

Author, Shaurya Karanbir Gurung; Title: "DRDO innovates automatic sanitizer and ultraviolet devices to fight coronoavirus"; Internet Published at least as early as Mar. 30, 2020., by the Economic Times, economictimes.indiatimes.com. Published in India.

Author: Nerd Techy;. Title: "Best Handheld Germicidal UV Light Wand 2020The UVLyzer' Sterilizes Any Surface in Mere Monments"; Internet Published at least as early as July at https://nerdtechy.com2020 by Nerd Techy.

* cited by examiner

PERSONAL, PORTABLE, HAND-HELD UV SANITIZER AND METHOD OF USE

CROSS-REFERENCE TO RELATED APPLICATIONS

This application claims the benefit under 35 US 119(c) of provisional patent applications: Ser. No. 63/021,254, filed May 7, 2020 and entitled "Personal Handheld, Reusable, Corona Virus UV Hand Sanitizer and Method; Ser. No. 63/030,368, filed May 27, 2020 and entitled "Safe, Portable UV Hand and. Surface Sanitizer and Method of Use"; Ser. No. 63/038,851, filed Jun. 14, 2020; and Ser. No. 63/047, 163, filed Jul. 1, 2020 and entitled "UV Hand and Surface Sanitizer Interfaceable with a Cellphone and Method of Use", all of which are hereby incorporated by reference.

BACKGROUND OF THE INVENTION

Field of the Invention

This invention generally relates to UV light sanitizers, and more specifically, to a personal, portable, handheld UV light sanitizer and method of use for safely sanitizing both a user's hand and target surfaces spaced from the sanitizer with UV light radiation.

Discussion of the Prior Art

It is well known, that ultraviolet radiation has a deleterious effect on viruses. Portable LV light sanitizers that radiate surfaces spaced from the person holding the portable device are well known. Examples of such portable ultraviolet radiation devices are shown in U.S. Pat. No. 6,579,495 issued. Jun. 17, 2003 to Maiden; U.S. Pat. No. 5,900,212 issued May 4, 1999 to Maiden et al. used to treat water, and patents, cited therein, all of which are hereby incorporated by reference.

Other examples of portable UV radiation devices are shown in Published U.S. patent applications 2015/0359915 of Farren et al. published Dec. 17, 2015; 2004/0256581 of Au et al. published Dec. 23, 2004; 2006/0079948 of Dawson published Apr. 13, 2006; 2007/0055195 of Browne published Mar. 8, 2007; 201610184467 of Cheng et al. published Jun. 30, 2016; 2017/0080116 of Kreiner et al. published Mar. 23, 2017; 2017/0216466 of Dujowich et al. published Aug. 3, 2017; 2006/0078484 of Greep published Apr. 13, 2006 and 2017/0157276 of Dobrinsky et al., published Jun. 8, 2017, all of which are hereby incorporated by reference While portable, unfortunately, none of these known devices are designed for, or are well adapted to, sterilizing a user's own hands and, in some of the units described in the above references, even special care is taken to avoid radiation of the user's hand or other skin surfaces.

In Published U.S. patent application 2019/011780 of Hishinuma et al. published Apr. 25, 2019, a hot air hand dryer incorporates a UV disinfection device. However, the hand dryer is fixedly attached to a wall, is not portable and is not designed to be carried in a user's hand and used at locations spaced from the hand dryer. Generally, such a fixedly attached hand dryer is only going to be used after a person has already washed their hands of any infectious virus, etc. and is of questionable actual benefit.

A portable, handheld UV light sanitizer is shown in U.S. Pat. No. 10,849,995 issued Dec. 1, 2020 to Crosby which may be held in a hand while being sanitized but due to the size, shape and configuration of the housing unsafe UV light leakage beyond the user's hand is not prevented. It appears that no provision is made to prevent excessive and thus unsafe radiation of the user's hand. Disadvantageously, this hand sanitizer may only be used to sanitize the user's hand and no other surfaces. A further problem is that due to the configuration of the housing and placement of the UV light sources, radiation is not uniformly distributed across a user's had when holding the sanitizer housing.

Generally, it is believe that all of the known portable UV hand sanitizers suffer from one or more defects that do not adequately protect the user from excessive and thus damaging radiation of a user's skin and are not suitable for both hand sanitizing and sanitization of non-skin surfaces spaced from the user's hand. Accordingly, sanitization can only occur after a user has already touched a pathogen coated surface and possibly already passed the pathogens to other parts of the user's body that may have been touched.

During the pandemic, available personal liquid hand sanitizers can quickly be used up and may not be easily replaced due to scarcity in the market because of and hording or excessive demand exceeding production and distribution capacity. Even when the pandemic is over, such personal liquid hand sanitizers, may once again become scarce if another virus arises or the Corona-19 virus or variant returns.

Accordingly, during this time of corona virus pandemic and shortages of liquid hand sanitizers, there is an urgent need to provide an alternative and convenient means that a person can carry to sanitize their hands after touching a surface, such as a door knob or grocery item suspected of harboring dangerous pathogens. their own hands that is easy to carry and can easily be used immediately after touching door handles, food items and other like surfaces that one may touch and which may be covered with dangerous microscopic virus and the like. There is also a need for a person to be able with the same device to sanitize a suspect surface prior to touching the surface to increase the chance of avoiding any infectious contact, whatsoever, with pathogenic viruses or bacteria.

SUMMARY OF THE INVENTION

It is therefore a general object of the present invention to provide a portable, personal, handheld UV sterilization device for personal use to sanitize both a user's hand holding the sanitizer and target surfaces spaced from the user's hand and the sanitizer and a method of use that that is both more efficacious and safer than known portable UV sanitizers.

More particularly, it is an object to provide a personal, portable, handheld UV light sanitizer, having an elongate tubular housing with a light transmittable outer wall having an outer surface extending between opposite housing ends, said tubular housing having a peripheral dimension approximately equal to the length of a user's hand measured from the tip of the thumb to the tip of the middle finger and a width approximately equal the width of a hand, said width and length enabling a user to grasp the tubular housing and substantially wrap their hands around and cover substantially the entire surface of the tubular housing with substantially the entirety of user's palm, fingers and thumb in intimate contact with the housing surface, a UV light source protectively contained within an interior of the tubular housing in a location to uniformly radiate UV light outwardly from the interior and through the light transmittable wall surface to uniformly impinge the skin surface of the user's hand when grasping the tubular housing with a palm and fingers and thumb of the user's hand wrapped substantially entirely around the tubular housing to sanitize substantially all the surface of the palm and inside surfaces of the fingers and thumb of the user's hand, a portable power source mounted within the housing and connectable with the LTV light source, means carried by the house for initiating energization of the UV light source for a single safe hand sanitization cycle time period when the user's hand is wrapped around the housing, and means for automatically controlling termination of energization of the UV light source to prevent excessive UV radiation of the user's hand.

Preferably, the energizing initiating means includes at least one of a UV light source switch carried at the outer surface of tubular housing energized by a user actuating a the UV light source switch while grasping the tubular housing intermediate the opposite ends. The single actuation switch is preferably recessed to avoid inadvertent actuation when the user is merely handling the sanitizer without the user's hand wrapped around the tubular housing. Alternatively, insuring that a user's hand is wrapped around the tubular housing when the UV light source is energized, multiple UV light source actuation microswitches connected in series circuit may be located at multiple positions around the periphery of the tubular housing that must be actuated by the user's hand simultaneously in order to initiate energization. Inadvertent energization of the UV light when the user's hand is not wrapped around the tubular housing may also be prevented by means employing multiple visible light sensors or infrared sensors carried around the tubular housing for sensing whether a user's hand is wrapped around the light transmittable tubular housing.

In the preferred embodiment, a pair of annular walls respectively located at the opposite ends may be provided to block stray UV light from radiating beyond the opposite ends, and masking means may be provided to block radial UV light leakage. The rearward one of the annular walls may also provide a bearing surface to prevent slippage from the user's hand, while the forward annular wall may provide suitable mounting for distance and skin sensors, actuation switches and indicator lights and audio speakers.

In order to limit UV radial light leakage, at least one of a resilient mask member mounted around the tubular housing, or a flexible mask member wrapped around the tubular housing masks may be provided if needed to cover any gaps between the edges of the user's hand and the ends of the light transmittable tubular housing. If a user's hand is longer than the girth, or peripheral length of the tubular housing, a UV light transmittable material secured to the outer surface of the tubular housing may be provided to increase the size of the girth to fit the user's hand.

Yet a further object of the invention is to also provide means carried by the housing for sanitization of non-skin surfaces spaced from the tubular housing and the hand of the user. Preferably, the non-skin surface sanitization means includes another UV light source located at one of the opposite ends of the tubular housing and positioned to radiate directed outwardly from the tubular housing in the elongate direction of the elongate tubular housing or in a direction transverse to the elongate direction, and a non-skin actuation switch carried by the body to energize the other UV light source with the portable power supply. Preferably energization of the one UV light source used to radiate the user's hand is prevented when the other UV light source is energized to radiate a suspect target spaced from the user.

Advantageously, for purposes of safety, the portable, handheld UV light sanitizer includes means sensing if the other UV light source is directed at a person's skin, and means for responsive to the sensing means for automatically deenergizing the second UV light source if skin is detected to prevent unintended or unsafe radiation of a user's skin without radiation time period limitations.

Further, preferably means are provided for preventing unsafe excessive radiation longer than a preselected maximum safe time period for a single energization of the UV light source and for preventing more than a preselected number of initiations of energization or durations of energization of the one LTV light source over a preselected, past, accumulative time period. Initiation of a hand sanitization cycle too soon after the end of an immediately prior successive hand sanitization cycle is also prevented.

Preferably, a range finder and means responsive to the range finder to adjust the intensity of the radiation, to provide an indication if a target surface is out of range or to automatically increase the power of the UV radiation is provided.

Another object of the invention is to provide a method for a user to safely use UV light radiation to reduce the risk of infection from pathogenic viruses or bacteria that may be on a suspect surface that a person wishes to touch or has touched, comprising the steps of (1) carrying a single handheld UV light sanitizer that may be used alternatively in either a hand sanitization mode of operation in either a non-skin surface sanitization mode or a skin surface sanitization mode with safety features to reduce the risks of excessive radiation of a user's skin, (2) prior to touching any suspect non-skin surfaces, actuating the UV light source in the non-skin surface sanitization mode to selectively radiate said suspect non-skin surfaces with sufficient intensity to kill or disable the pathogens that may be harboring on said non-skin target surfaces, and (3) after touching any suspect non-skin surfaces with a user's hand, actuating the UV light source in a skin surface sanitization mode to radiate the user's hand.

Preferably, the method includes the step of preventing unsafe excessive radiation of the user's skin by limiting at least one of (1) a single hand sanitization cycle time period measured between the time of initiation of energization of the UV light source and the automatic termination of energization after a preselected maximum preselected time period has lapsed, or (2) the number of energizations during a preselected past time period exceed a preselected safe member.

Yet, a further object of the invention is to provide a method of sanitizing a surface with a personal, portable, hand-held UV light sanitizer, by performance of the steps of (1) directing a UV light source of the sanitizer at a target surface to be sanitized, (2) selectively energizing the UV light source to radiate the target surface with UV light radiation, (3) sensing a target distance signal from the sanitizer indicating whether the target surface distant for the UV light source for the radiation intensity at the surface to be of sufficient strength to kill or disable pathogenic viruses or bacteria on the target surface and (4) responding to the target distance signal as necessary to locate the UV light source sufficiently close to the target surface to ensure that the radiation intensity is sufficient to kill or disable pathogenic viruses or bacteria on the target surface.

Preferably, target distance signal is one of a visual light signal, an audio signal or a tactile vibration signal. It may be the color of a visible light source that is directed at the target surface to radiate the target surface with visible light also being radiated with UV light.

Still, another objective of the invention is provision of a method of safely sanitizing a non-skin surface with a personal, portable, hand-held UV light sanitizer, by performance of (1) energizing a UV light source to radiate a surface at which the UV light source may be directed, (2) sensing with an infrared light sensor if the UV light source has been inadvertently directed at a skin surface, (3) and (3) automatically deenergizing the UV light source in response to skin surface sensing means sensing that the UV light source is directed at a skin surface. Preferably, the step of sensing is performed by sensing infrared radiation.

One more objective of the invention is to provide a method of safely sanitizing a user's skin with a personal, portable hand-held UV light sanitizer, comprising the steps of (1) initiating energization of a UV light source while directed at a user's skin to radiate the use skin with UV light radiation, (2) automatically terminating energization of the UV light source after a preselected maximum sanitization cycle time period and (3) automatically preventing energization of the UV light source whenever the total radiation time during a prior preselected prior time period exceeds a preselected maximum safe total radiation time.

BRIEF DESCRIPTION OF THE DRAWING

The forgoing objects, features and advantages will be described in greater detail and further objects, features of the invention will be made apparent from the following detailed description made with reference to the several figures of the drawing in which.

DETAILED DESCRIPTION

Figure 1:
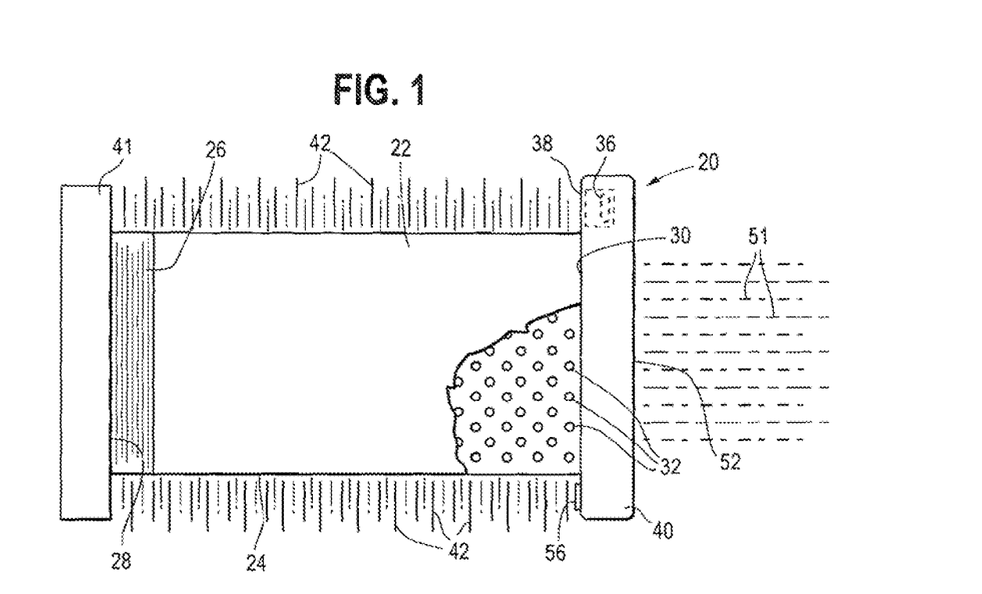
FIG. 1 is a side elevation view of one form of the personal, portable, handheld UV light sanitizer of the present invention showing the light transmittable tubular housing and outwardly extending annular light blocking members at opposite ends of tubular housing.
Figure 2:
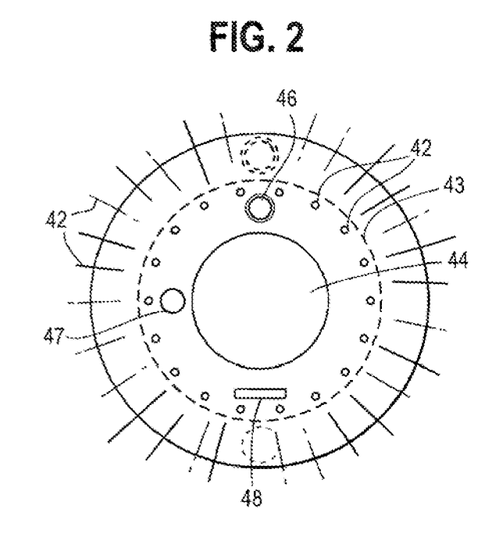
FIG. 2 is an elevation end view of the rearward end of the UV light sanitizer of FIG. 1 showing the rearward, annular light blocking member that also carries battery charging ports and an access hatch for access to a removable battery.
Figure 3:
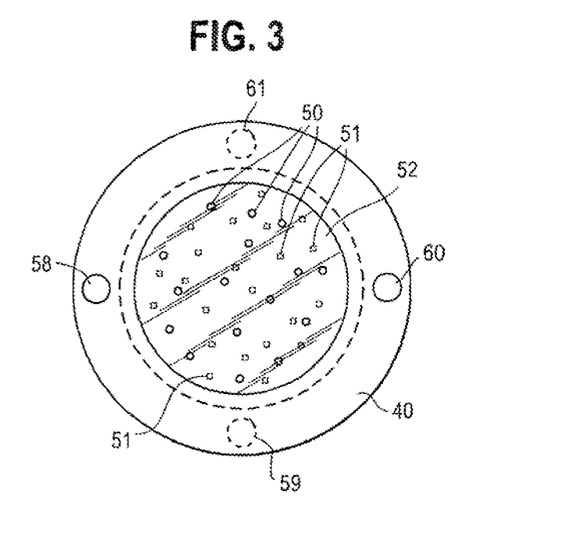
FIG. 3 is an elevation view of the forward, UV light emitting front end of the UV light sanitizer of FIG. 1 located opposite the back end shown in FIG. 2.

Referring to FIGS. 1-3, a preferred embodiment of the portable, personal, handheld UV light sanitizer 20 of the present invention is seen to have an elongate tubular housing 22. Preferably, the cross-section of the tubular housing is circular, as shown in FIGS. 2 and 3. Alternatively, the tubular housing has an oval shape that will fit snuggly with a user's hand.

The tubular housing 22 has an outer wall 24 that is light transmittable, i.e. transparent or translucent, to ultraviolet, or UV, light. Preferably, the entire length of the outer wall 24 is made of clear, uncolored light transmittable shatterproof glass, such as shatterproof quartz glass. Alternatively, a clear plastic may be used.

Figure 4:
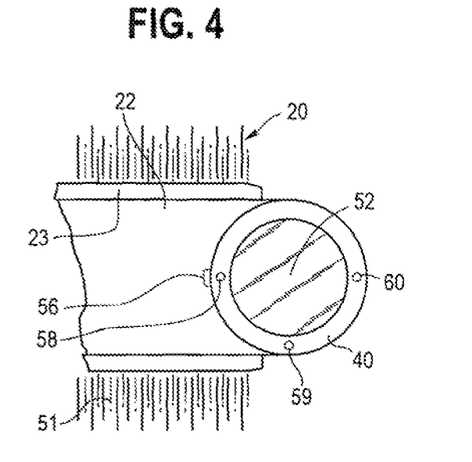
FIGS. 4 and 5 are a bottom view and side view, respectively, in which the light emitting end at the front of the tubular housing is directed in a direction transverse to the elongate direction of the tubular housing instead of in the elongate direction as shown in FIG. 1.
Figure 5:
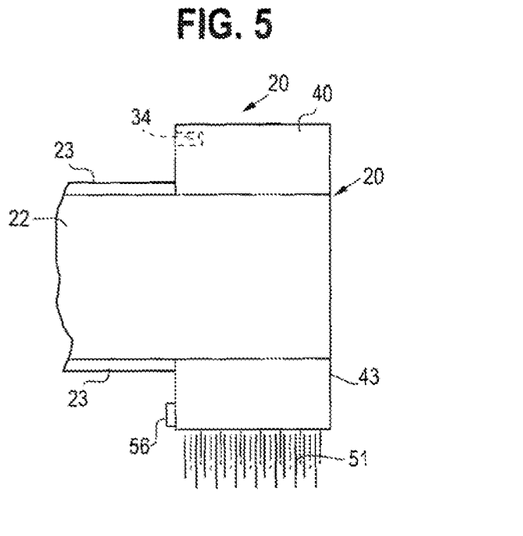

The light transmittable outer wall 24 has a peripheral dimension, or girth, measured around the outer wall 24 that is approximately equal to the length of a user's hand measured from the heal, or back, of the palm to the tip of the middle finger and a width approximately equal the width of a hand of such length. The sanitizer 20 may be provided in different sizes to accommodate hands of different size. If not, then the girth is selected for the smallest hands, and then, if needed, a UV light transmittable material 23 is either wrapped around or otherwise fitted around the outer wall 24, such as shown in FIGS. 4 and 5, to fit to a longer hand.

Figure 7:
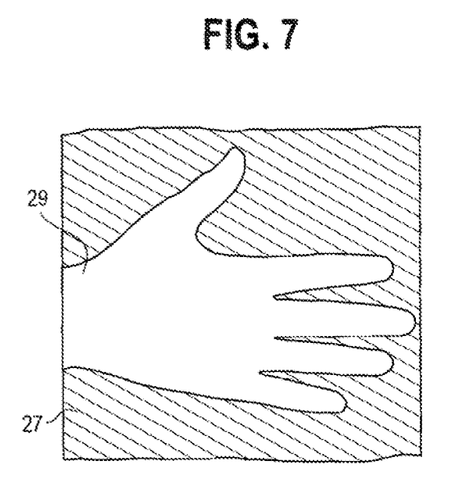
FIG. 7 is a schematic illustration of a personalized masking member providing a radiation opening conforming to the shape of a user's hand.

If the width of the tubular housing is wider than the width of a user's hand, then an opaque UV light blocking, or masking, width adjustment member 26 is fitted around the tubular housing 24. The width of the UV light blocking member 26 is selected to block UV light from the back end 28 to the outside edge of the user's palm and little finger when grasping the tubular housing 24 with the thumb and forefinger at the front end 30. Referring to FIG. 7, alternatively a mask 27 with an opening 29 conforming to a user's hand may also be mounted around the tubular body 22.

Whether the girth and light transmittable length are adjusted to fit or selected to fit the user's hand, the size of the tubular housing 22 enables a user to grasp the tubular housing 22 and substantially wrap their hands around and cover substantially the entire surface of the tubular housing to substantially enable intimate contact with the housing surface 24. When the user is grasping sanitizes in such a manner, uniform UV radiation form a source within the tubular housing 22 of substantially the entirety of user's palm, fingers and thumb is achievable. tubular housing.

The UV light is preferably generated by a plurality of UV light sources, such as UV light emitting light emitting diodes, or UV LEDs, 32 (hereinafter "UV light source 32), protectively contained within the interior of the tubular housing 22 and uniformly distributed around or uniformly spaced from the inside surface of the outer wall 24. In either event, the UV LEDs uniformly radiate UV light outwardly from the interior of the tubular housing 22 and through the light transmittable outer wall 24 to uniformly impinge the skin surface of the user's hand when grasping the tubular housing 24 to sanitize substantially all the surface of the palm and inside surfaces of the fingers and thumb of the user's hand. Alternatively, UV LEDS may be imbedded within the light transmittable outer wall 24.

Figure 8:
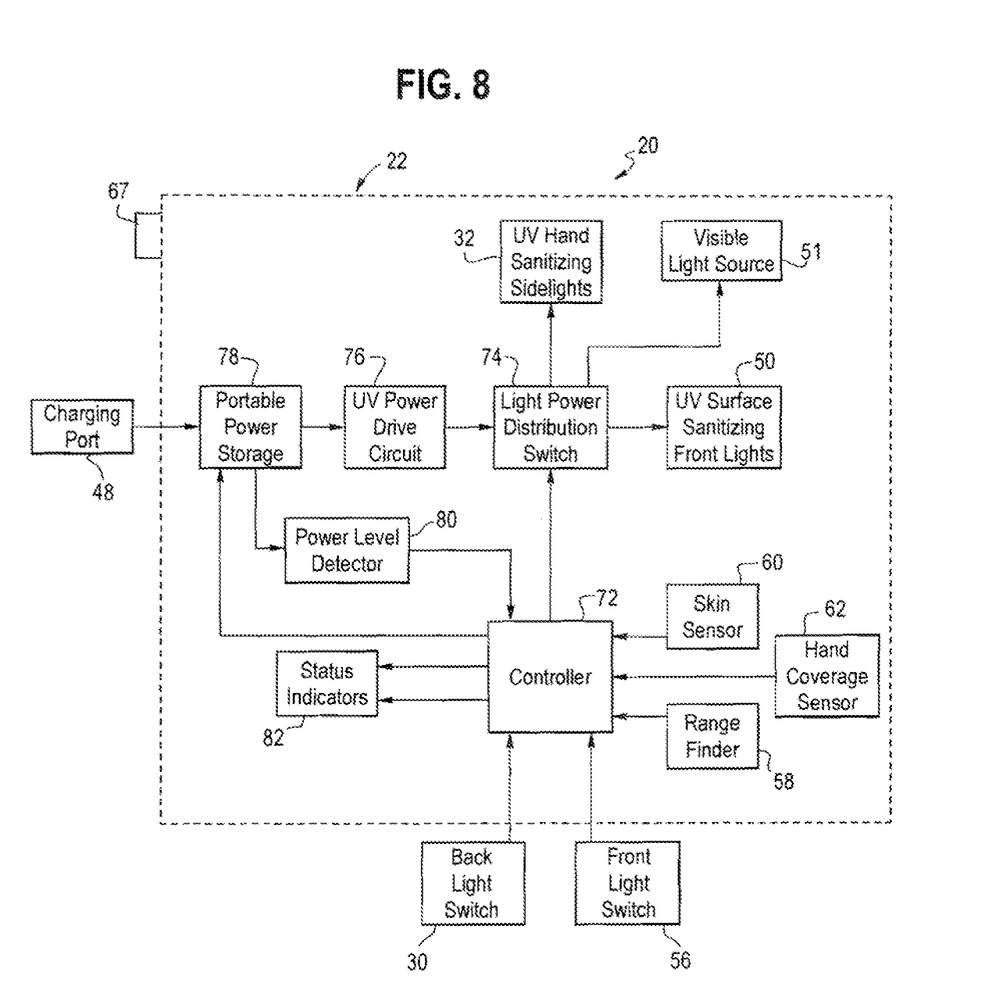
FIG. 8 is a functional block diagram of the personal, portable, handheld UV light sanitizer of FIGS. 1-6.

A removable and rechargeable battery or other portable power source 78, FIG. 8, is protectively mounted within the housing and connectable with the UV light source to energize, or turn on, the UV light source 32 and a visible light source shown. Referring to FIG. 2, in the back end 43 of the rearward annular member 41, a removable battery hatch cover 44 is provided to enable access to the removable battery for purposes of replacement. The battery, capacitor or other like DC electrical storage device is preferably rechargeable, and for that purpose at least one of a coaxial charging port 46 and a USV charging port 48 are provided.

Also, located at the back may be a power switch 47, but preferably the sanitizer is constantly in a low power state monitoring whether either of the switches 36 or 56 has been activated, as shown in the flow chart of FIG. 8.

Initiation of a UV light hand sanitization cycle is achieved by a user actuating a hand sanitization cycle switch 36 carried at an inner surface of a forward annular, light blocking member 40. A rearward, or back, annular outwardly extending UV light blocking member 41 is also provided at the opposite back end 28 of the tubular housing 24 which also provides a bearing surface to reduce the risk of the sanitizer 20 slipping from the user's grasp.

The switch 36 is preferably either a touch contact switch or a spring-loaded mechanical push button switch. In either event, the switch is recessed in a backwardly opening, switch recess 38 to prevent inadvertent actuation when a user is grasping or otherwise handling the UV light sanitizer. Alternatively, a mechanical push button switch is used with a spring bias to a closed position that is sufficiently strong to prevent inadvertent actuation.

Figure 6:
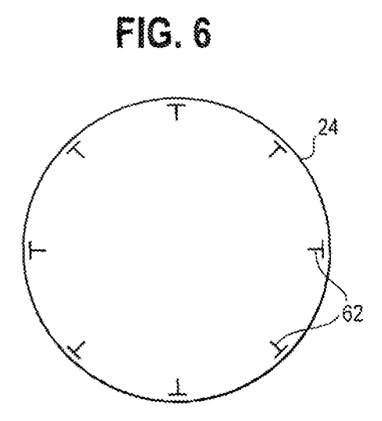
FIG. 6 is a schematic illustration of hand coverage sensing detectors that determine when a hand is substantially wrapped around the tubular housing.

Referring to FIG. 6, preferably a plurality of light sensors 62 are provided inwardly of the outer surface and distributed along the length and around the periphery of the outer wall 24 to sense light being transmitted inward into the tubular body 24. Signals from these light sensors are used to automatically determine whether or not the user's hand is wrapped around the tubular body 24. In case of the sensors 62 being infrared sensors, they sense infrared radiation from the user's hand if the hand is wrapped and do not sense infrared light if the hand is not wrapped around the tubular body. In the case of the sensors being visible light sensors, sensing of visible light coming into the tubular body 22 indicates that the tubular body is not being covered by the user's hand to block the incoming light.

Alternatively, the tubular housing outer surface is made of flexible, resilient material multiple UV light source switches with plurality of embedded, or otherwise engageable, microswitches distributed around the outer surface 24. The multiple switches are connected in series circuit such that all the UV light source switches must be actuated by the user's hand simultaneously in order to initiate energization to prevent inadvertent. Embedded strain gages may also be used to sense when a user's hand is gripping the tubular housing 24.

In any event, when the hand cycle switch 36 is actuated the UV light source 32 is energized and UV hand sanitization radiation 42 is emitted uniformly outwardly from the outer wall 24 to uniformly radiate the user's hand for a preselected safe hand radiation time period that has been determined safe and nondamaging to the user's skin. Generally, a period of five to twelve seconds is preferred, and the intensity of UV radiation is selected according to the radiation time period with increases in time yielding decreases in intensity and vice versa. If means are provided to enable a user to change the hand cycle radiation time period, then means are provided to automatically change the level of radiation. The radiation intensity versus time setting for safe radiation cycles depends upon dimensions of the sanitizer 20.

An important advantage of the present sanitizer 20 versus other portable sanitizers when related to hand sanitizing is that, unlike many portable sanitizers that could be used by radiating a hand spaced from the UV light source, the distance from the UV light source in the sanitizer 20 is a known distance, such that that it is impossible for the user's hand to be either too close to the UV light source to be safe, because the radiation is then too intense to be safe, or too far away to be effective, because of the intensity then being too low to be fully effective at disabling pathogens on the user's hand.

Preferably, the UV hand sanitizer 20, in addition to functioning to sanitize a user's hand, is also capable of sanitizing non-skin surfaces spaced from the sanitizer 20 and the user's hand. For that purpose, another UV light source, preferably again in the form of an evenly distributed array of UV LED's 50, are mounted at a front UV light transmittable wall 52 at the forward end of the sanitizer 20. The UV light source 50 radiates UV light 54 in a direction away from tubular housing 22.

In addition to the UV light source 50, a visible light source, preferably, an evenly distribution array of visible LED's 51 (hereinafter visible light source 51), is provided intermingled with and pointed in the same direction as the UV light source 50. The UV light source 51 is energized whenever the UV light is energized to illuminate the target surface at which the UV light source is directed to identify by visual illumination of the target source. The coler of the visible light source 51 as illuminated on the target surface may be controlled to provide a varying indication of range. For instance, when the target is in range the visible light may tend toward greens and blues, while red or orange when the target may be out of effective range.

Figure 9:
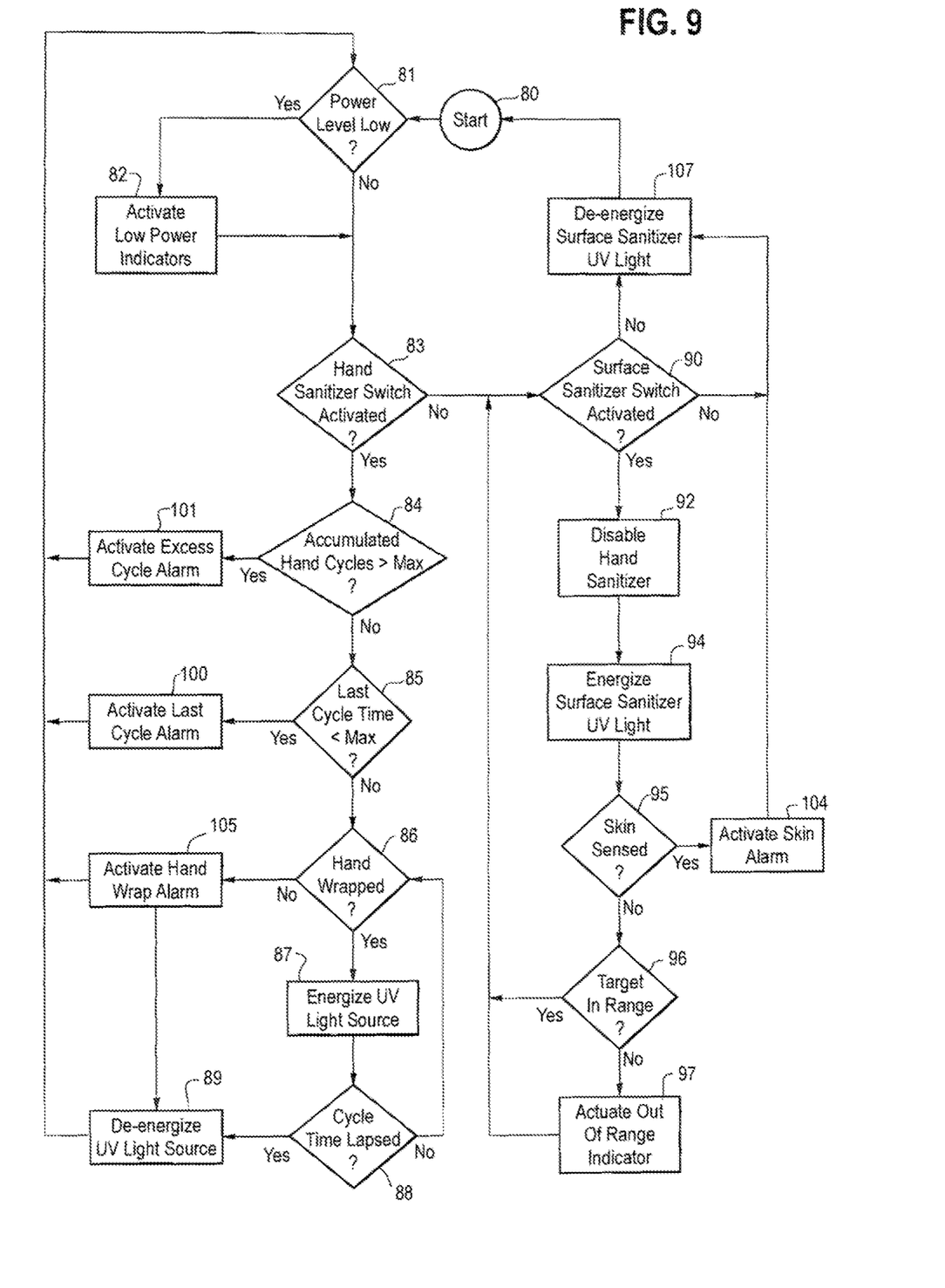
FIG. 9 is a logic flow chart of the software control program in the microprocessor controller of FIG. 8.

Referring to 8, with references also to FIGS. 1-3, the microprocessor controller 72 is operated in accordance with a software program that function according to, the illustrated logic flow chart. The program rapidly recycles repetitively through program start 80, as follows:

After start, a decision is made in step 81 as to whether the power level sensor 80 is providing an indication that the power remaining in the portable power supply 78 is low. If the power level is low, then in action step 82, the controller 72 activates the appropriate one of the status indicators 59 or 61 to provide a low battery indication. Preferably, indicator light 61 will emit a light indicative of the low battery condition. Alternatively, a low power indicative tone is caused to be emitted from the status indicating speaker 59.

After a determination is made concerning power level and an indication is provided or not, a decision is made whether the hand sanitizing mode switch 36 has been actuated. If the switch 36 has been actuated, then the program moves through a series of decisions to prevent excessive skin irradiation beginning with step. If not, the program moves to step 90 to decide whether the non-skin surface sanitization mode switch 56 has been operated.

Presuming that the hand sanitizing mode switch has been actuated, then the programs moves to decision step 84 where it is decided whether the number of past hand sanitization cycles during one or more a past preselected period exceeds a preselected maximum number for such period, such that another hand sanitization cycle would be excessive for the past preselected time period. For instance, maximum number of cycles per hour may not exceed three or four, while the maximum number of cycles in one day may, or the past twenty-four hours may not be greater than twenty-four. This decision is made pursuant to the logic flow chart of FIG. 10, described below.

If the preselected maximum number has been exceeded, then the UV light source is not energized for another hand sanitization cycle. Instead, in step 101 a warning indication of the overage is provided via the speaker 59 or the status light 61 and the program returns to start 80. The warning indication may be a voice message transmitted through the speaker 59 advising when sufficient time will have passed to enable performance of another hand sanitization cycle.

If the preselected, accumulated number of hand sanitization cycles has not been exceeded for any of the given time periods, the program moves to decision step 85 where it is determined whether the time passed since the last hand sanitization cycle was completed is less than a minimum safe time period such as five to twenty seconds. If so, then a minimum pause time warning is provided in step 100. The user then only has to wait the short minimum time period between cycles to once again be enabled to energize the UV light source with switch 36. The program then returns to start 80.

If the minimum permitted time between successive hand sanitization cycles had not been exceeded, then the program moves to step 86 where it is determined by the microprocessor controller 78 in response to hand coverage sensors 62, whether a user's hand is sufficiently wrapped around the tubular housing 22 to provide substantial coverage and minimum UV light leakage. If the sensors 62 indicate there is not good coverage, then in action step 105, a hand wrap alarm is provided and the program returns to start 80. If there is good hand coverage, then the program moves to action step 87 where the hand radiating UV light source 32 is finally energized.

The program then moves to decision step 88 where it is determined whether a preselected maximum single hand sanitization cycle time has passed. If not, the program recycles to step 88, but if so, the program moves to step 89 to deenergize the UV light source 32 and then return to start 80.

From start 80, the program once again moves to step 83, and if it is decided that the hand sanitization switch 36 has not been activated, the program goes to decision step 90 where it is determined whether the non-skin target service sterilization mode switch 56 is being held in an actuated state. If not, then the program moves to action step 98, where, if previously energized, the surface sanitization UV light source 50 is deenergized On the other hand, if the switch 56 is being actuated by the user, then the program moves to action step 92, where the hand sanitization switch 36 is disabled from energizing the hand radiating light source 32. Next, in action step 94 the non-skin surface sanitization UV light source 50, if not previously energized, is then energized. Thus, the UV light source remains energized only so long as the user holds the switch in an actuated state. Since the target surface is not skin, there is no maximum time limit that needs to be imposed for safety, but am indication of excessive radiation my be provided if the actuation switch remains activated for longer than a preselected maximum period believed excessive and needlessly wasteful of battery power.

Then, in decision step 95, a determination is made if skin is being sensed by the infrared sensor 60, and if so, in action step 104, a visual or audible warning is given, and the program moves to action step 98, where the surface sanitization UV light source is deenergized. The program then returns to start 80.

If skin is not sensed, the program then moves to action step 96 where, in response to signals from the range finder 58, the controller 72 decides if the target surface at which the surface sanitization UV light source 51 is directed is within the maximum effective distance to kill pathogens on the target surface. If not, then in action step 97, a suitable visual or audible signal is provided to the user, but the program returns to decision step 90 to determine if the surface sanitization switch, is still being held in actuated state.

Figure 10:
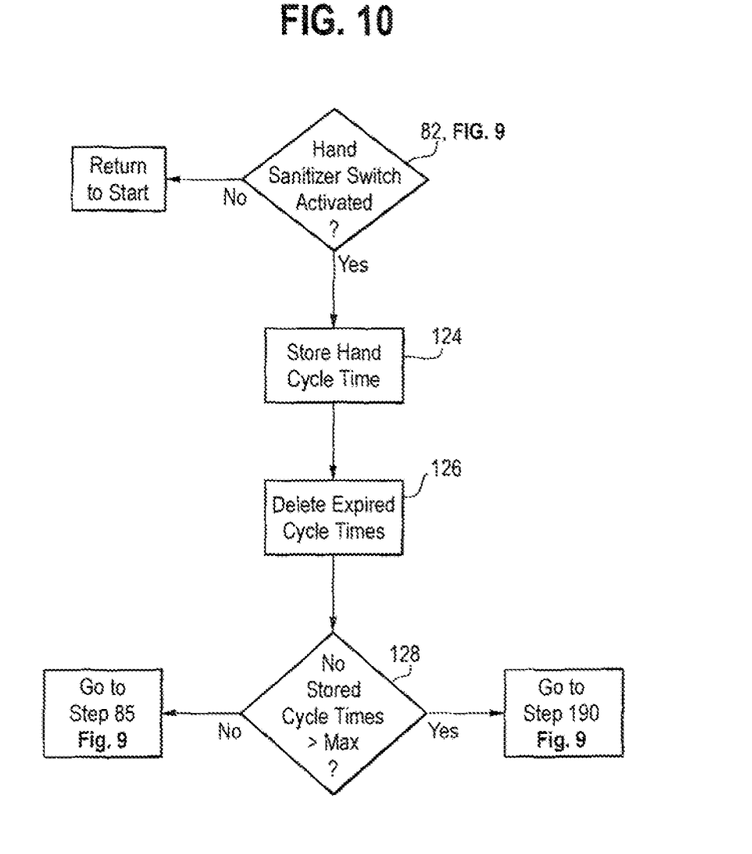
FIG. 10 is a logic flow chart of a subroutine of the program of FIG. 9 used to determine if there have been too many past hand sanitization cycles to safely perform another cycle.

Step 84 of the logic flow chart of FIG. 9, at which it is determined whether the number of accumulated hand sanitization cycles over a preselected past time period or time periods has exceeded a preselected maximum number deemed to be safe is performed pursuant to the logic flow chart of FIG. 10. Referring to FIG. 10, if it is determined in decision step 83 of FIG. 9 that the hand sanitization switch 36, FIG. 1, has been actuated, then in action step 124, the current time that the sanitization switch was actuated is stored in memory of the microprocessor 72. Next, in action step 126, stored skin radiation cycles that were stored greater than a preselected maximum time period and are expired are deleted from memory. Then in decision step 128, a determination is made whether there remain a number of stored cycle times greater than a preselected maximum number. If so, the program goes to step 101 of FIG. 9. If not, then the program moves to step 85 of FIG. 9.

While the invention has been described in detail with respect to a particular embodiment that is preferred, it should be appreciated that many functional variations may be provided without departing form the spirit and scope of the invention as defined in the claims.

The invention claimed is:

1. A personal, portable handheld UV light sanitizer for sanitizing a user's hand having a thumb with a tip, a middle finger with a tip and a width of a preselected length measured from the tip of the thumb to the tip of the middle finger and a palm with a preselected width, comprising:
    a housing having an interior, a pair of opposite ends and an elongate, tubular, UV light transmittable outer wall extending between the pair of opposite ends of the housing;
    said outer wall having a peripheral dimension approximately equal to the preselected length of the user's hand and a length measured between the opposite ends equal to the preselected width of the user's hand, said peripheral dimension and length enabling the user to grasp the tubular housing with the user's hand and substantially cover the entire surface of the outer wall with the user's palm, fingers and thumb in intimate contact with the UV light transmittable outer wall
    a skin sanitizing UV light source protectively contained within the interior of the tubular housing in a location to uniformly radiate UV light outwardly from the interior and through the UV light transmittable wall to uniformly impinge substantially all skin surface of the user's hand when grasping the tubular housing with a palm and fingers and thumb of the user's hand wrapped around the tubular housing to sanitize the user's hand;
    a portable, electrical power source mounted within the housing and connectable with the UV light source;
    means carried by the tubular housing for initiating energization of the skin sanitizing UV light source with the portable power source, for a single preselected radiation cycle time period less than that which could cause radiation injury to the user's hand when the user's hand is wrapped around the outer wall, and
    means for automatically terminating energization of the UV light source at the end of the radiation cycle time period to prevent excessive radiation of the user's hand.

2. The personal, portable handheld UV light sanitizer of claim 1 in which the energizing initiating means includes at least one of
    a UV light source switch carried at the outer surface of the tubular housing and actuatable by a user's finger to actuate the skin sanitization UV light source switch when grasping the tubular housing intermediate the opposite ends, multiple UV light source switches surrounding the surface of the tubular housing on opposite sides and connected in series circuit such that all the UV light source switches must be actuated by the user's hand simultaneously in order to initiate energization, multiple visible light sensors carried around tubular housing for sensing whether a user's hand is blocking visible light positioned around the tubular housing;

means responsive to all the multiple visible light sensors being blocked to initiate or enable energization;

infrared sensors carried around tubular housing for sensing infrared radiation from a user's hand when positioned around the tubular housing; and means responsive to all the multiple infrared sensors sensing infrared radiation from the user's hand visible light sensors being blocked to initiate or enable energization.

3. The personal, portable, handheld UV light sanitizer of claim 2 in which the switch is recessed to prevent inadvertent actuation by the finger of a user.

4. The personal, portable, handheld UV light sanitizer of claim 1 including a pair of annular walls respectively located at the opposite ends of sufficient outward extent to block stray UV light from leaking radiation beyond the opposite ends.

5. The personal, portable, handheld UV light sanitizer of claim 1 including means carried by the housing for sanitization of non-skin surfaces spaced from the tubular housing and the hand of the user.

6. The personal, portable, handheld UV light sanitizer of claim 5 in which the non-skin surface sanitization means includes a non-skin surface UV light source located at one of the opposite ends of the tubular housing and
positioned to radiate directly outwardly from the tubular housing in elongate direction of the elongate tubular housing, or
positioned to radiate directly outwardly from the tubular housing in a direction transverse to the elongate direction of the elongate tubular housing, and a non-skin sanitization actuation means carried by the tubular housing to energize the non-skin UV light source with the portable power source.

7. The personal, portable, handheld UV light sanitizer of claim 6 including a range finder for determining distance to a target surface, and
means responsive to the range finder to
adjust the intensity of the UV light radiation from the non-skin surface UV light source directly with the distance to the target surface, and
provide an indication if a target surface is out of range.

8. The personal, portable, handheld UV light sanitizer of claim 6 including an infrared detector for detecting infrared radiation from the target surface, and
means responsive to the infrared detector sensing infrared radiation indicating that the target surface is a person's skin to automatically deenergize the other light source.

9. The personal, portable, handheld UV light sanitizer of claim 6 including means for preventing energization of the skin sanitizing UV light source used to radiate the user's hand when the non-skin sanitizing UV light source is energized to radiate a suspect target spaced from the user.

10. The personal, portable, handheld UV light sanitizer of claim 6 including means for sensing if the non-skin surface UV light source is directed at a person's skin, and
means for responsive to the sensing means for automatically deenergizing the non-skin surface UV light source if skin is detected.

11. The personal, portable, handheld UV light sanitizer of claim 10 in which the sensing means is an infrared detector carried at the one of the opposite ends of the housing and directed to sense infrared radiation from any target surface at which the non-skin surface UV light source is directed.

12. The personal, portable, handheld UV light sanitizes of claim 1 including means for preventing more than a preselected number of initiations of energization or durations of energization of the LTV light source over a preselected, past, accumulative time period.

13. The personal, portable, handheld UV light sanitizer of claim 1 including means for preventing two successive initiation of energizations if occurring within a time period less than a preselected minimum time period.

14. The personal, portable, handheld UV light sanitizer of claim 1 including means for blocking UV radiation from the tubular housing which the UV light blocking means including at least one of
a resilient blocking member mounted around the tubular housing to cover a selected end portion, and
a flexible member wrapped around the tubular housing to cover a selected end portion, and
a mask wrapped around the tubular housing and having an opening conforming to the user's hand.

15. The personal, portable, handheld UV light sanitizer of claim 1 including means entirely surrounding the tubular housing for uniformly increasing the girth of the tubular housing.

16. The personal, portable, handheld UV light sanitizer of claim 15 in which the girth increasing means includes a UV light transmittable material secured entirely around the outer surface of the tubular housing.

17. The personal, portable, handheld UV light sanitizer of claim 1 in which the housing has a cross section that is one of
circular, or
oval.

18. A method for a user to safely use the UV light sanitizer of claim 1 to reduce the risk of infection from pathogenic viruses or bacteria, in which the sanitizer has a second UV light source that radiates outwardly away from the housing through a light transmittable wall spaced from the UV light transmittable outer wall to radiate surfaces with UV light spaced from the user's hand and means for selectively energizing the second UV light source
comprising the steps of:
carrying the UV light sanitizer;
prior to touching any suspect non-skin surfaces, energizing the second UV light source to selectively radiate said suspect non-skin surfaces with sufficient intensity to kill or disable the pathogens that may be harboring on said non-skin target surfaces; and
after touching any suspect non-skin surfaces with a user's hand, actuating the UV light source safely radiate the user's hand through the light transmittable wall.

19. A method using the sanitizer of claim 1 to sanitize a surface, comprising the steps of:
directing the UV light source of the sanitizer at a target surface to be sanitized;

selectively energizing the UV light source to radiate the target surface with UV light radiation;

sensing a target distance signal from the sanitizer indicating whether the target surface distant for the UV light source for the radiation intensity at the surface to be of sufficient strength to kill or disable pathogenic viruses or bacteria on the target surface; and responding to the target distance signal as necessary to locate the UV light source sufficiently close to the target surface to ensure that the radiation intensity is sufficient to kill or disable pathogenic viruses or bacteria on the target surface.

20. The method of claim 19 in which the target distance signal is one of a visual light signal, an audio signal or a tactile vibration signal.

21. The method of claim 20 in which the target distance signal is the color of a visible light source that is directed at the target surface to radiate the target surface with visible light also being radiated with UV light.

22. A method of using the sanitizer of claim 1 to safely sanitize a non-skin surface, comprising the steps of:

energizing the UV light source to radiate a surface at which the UV light source may be directed;

sensing with an infrared light sensor if the UV light source has been inadvertently directed at a skin surface; and automatically deenergizing the UV light source in response to skin surface sensing means sensing that the UV light source is directed at a skin surface.

23. The method of claim 22 in which the step of sensing is performed by sensing infrared radiation.

24. A method of safely sanitizing a user's skin with the personal, portable hand-held UV light sanitizer of claim 1, comprising the steps of:

initiating energization of the UV light source while directed at a user's skin to radiate the user's skin with UV light radiation;

automatically terminating energization of the UV light source after a preselected maximum sanitization cycle time period;

automatically preventing energization of the UV light source whenever the total radiation time during a prior preselected prior time period exceeds a preselected maximum safe total radiation time; and automatically preventing energization of the UV light source if a minimum length of time has not passed since an immediately prior energization.

25. The personal, portable, handheld UV light sanitizer of claim 6 including
a visible light source for illuminating a target surface, and
means for energizing the visible light source whenever the non-skin surface UV light source is energized.

26. The sanitizer of claim 25 including a means for preventing excessive radiation of the user's skin by limiting at least one of
a single hand sanitization cycle time period,
a time period between successive skin sanitization cycles, and
a number of energizations during a preselected past time period.

27. A method for a user of the personal, portable, handheld UV light sanitizer of claim 25 to use UV light radiation from the sanitizer to reduce the risk of infection from pathogenic viruses or bacteria that may be on a suspect surface that a person wishes to touch or has already touched, comprising the steps of:
illuminating the target surface with the visible light source, and
energizing the visible light source whenever the non-skin surface UV light source is energized.

28. A method for a user of the personal, portable, handheld UV light sanitizer of claim 6 to use UV light radiation from the sanitizer to reduce the risk of infection from pathogenic viruses or bacteria that may be on a suspect surface that a person wishes to touch or has already touched, comprising the steps of:
carrying the handheld UV light sanitizer in a hand of the user;
prior to touching any suspect non-skin surfaces, actuating the non-skin surface UV light source in the non-skin surface sanitization mode to selectively radiate said suspect non-skin surfaces with sufficient intensity to kill or disable the pathogens that may be harboring on said non-skin target surfaces; and
if, after touching any suspect non-skin surfaces with the user's hand, actuating the skin sanitizing UV light source in a skin surface sanitization mode to radiate the user's hand when grasping the tubular body.

29. The method of claim 27 including the steps of
preventing unsafe excessive radiation of the user's skin by limiting at least one of
a single hand sanitization time period,
the minimum time between successive skin sanitization cycles, and
the number of energizations during a preselected past time period.

30. A method for a user of the personal, portable, handheld UV light sanitizer of claim 6 to use UV light radiation from the sanitizer to reduce the risk of infection from pathogenic viruses or bacteria that may be on a suspect surface that a person wishes to touch or has already touched, comprising the steps of:
directing the non-skin surface UV light source of the sanitizer at a target surface to be sanitized;
selectively energizing the non-skin surface UV light source to radiate the target surface with UV light radiation;
sensing a target distance signal from the sanitizer indicating whether the target surface distance for the non-skin surface UV light source for the radiation intensity at the surface to be of sufficient strength to kill or disable pathogenic viruses or bacteria on the target surface; and
responding to the target distance signal as necessary to locate the non-skin surface UV light source sufficiently close to the target surface to ensure that the radiation intensity is sufficient to kill or disable pathogenic viruses or bacteria on the target surface.

31. The method of claim 29 in which a target distance signal is one of a visual light signal, an audio signal or a tactile vibration signal.

32. The method of claim 29 in which a target distance signal is the color of a visible light source that is directed at the target surface to radiate the target surface with visible light also being radiated with LTV light.

33. A method for a user of the personal, portable, handheld UV light sanitizer of claim 6 to use UV light radiation from the sanitizer to reduce the risk of infection from pathogenic viruses or bacteria that may be on a suspect surface that a person wishes to touch or has already touched, comprising the steps of:
initiating energization of the skin sanitizing UV light source while directed at a user's skin to radiate the user's skin with UV light radiation; automatically terminating energization of the skin sanitizing UV light source after a preselected maximum sanitization cycle time period; automatically preventing energization of the skin sanitizing UV light source whenever the total radiation time during a prior preselected prior time period exceeds a preselected maximum safe total radiation time; and automatically preventing energization of the skin sanitizing UV light source if a minimum length of time has not passed since an immediately prior energization.

* * * * *